United States Patent [19]

Mihailovski

[11] 4,206,141

[45] Jun. 3, 1980

[54] PROCESS FOR PREPARATION OF DI-SUBSTITUTED CYANAMIDES USING QUATERNARY SALT CATALYSIS

[75] Inventor: Alexander Mihailovski, Kensington, Calif.

[73] Assignee: Stauffer Chemical Company, Westport, Conn.

[21] Appl. No.: 969,910

[22] Filed: Dec. 15, 1978

[51] Int. Cl.$^2$ .......................................... C07C 125/08
[52] U.S. Cl. ................................. 260/551 C; 252/426
[58] Field of Search ..................... 260/551 C; 252/426

[56] References Cited

U.S. PATENT DOCUMENTS

| | | | |
|---|---|---|---|
| 1,659,793 | 2/1928 | Vliet | 260/551 C |
| 2,858,338 | 10/1958 | Speziale | 260/551 C |
| 3,692,832 | 9/1972 | Rider | 260/551 C |
| 3,992,432 | 11/1976 | Napier et al. | 260/465.1 |

FOREIGN PATENT DOCUMENTS

| | | | |
|---|---|---|---|
| 45-32686 | 10/1970 | Japan | 260/551 C |
| 46-2494 | 1/1971 | Japan | 260/551 C |
| 278681 | 11/1970 | U.S.S.R. | 260/551 C |

OTHER PUBLICATIONS

Vliet, Org. Syn., Collected vol. I, 203–204 (1932).
Donnetti et al., Tetr. Letters 39, 3327–3328 (1969).

*Primary Examiner*—Thomas A. Waltz
*Attorney, Agent, or Firm*—M. Henry Heines

[57] ABSTRACT

An improved process for the di-substitution of cyanamide is disclosed which comprises reacting a compound having the formula $$R^1X$$

in which $R^1$ is a member selected from the group consisting of $C_1$–$C_6$ alkyl, $C_2$–$C_6$ alkenyl, $C_2$–$C_6$ alkynyl, $C_7$–$C_{10}$ phenylalkyl, and $C_7$–$C_{10}$ halophenylalkyl, and X is halogen, with cyanamide in the presence of an aqueous solution of an alkali metal or alkaline earth metal hydroxide and a catalytic amount of a catalyst having the formula $$(R^2R^3R^4R^5M)^+Y^-$$

in which $R^2$, $R^3$, $R^4$, and $R^5$ are independently $C_1$–$C_{25}$ alkyl, M is selected from the group consisting of nitrogen, phosphorus, and arsenic, and Y is halogen.

11 Claims, No Drawings

PROCESS FOR PREPARATION OF DI-SUBSTITUTED CYANAMIDES USING QUATERNARY SALT CATALYSIS

BACKGROUND OF THE INVENTION

Di-substituted cyanamides are useful intermediates for the synthesis of symmetrical secondary amines. Unfortunately, this method of obtaining secondary amines is handicapped by the lack of a practical method for preparing di-substituted cyanamides.

In a procedure reported by E. B. Vliet, *Organic Synthesis, Collective Vol.* I, 203–4 (1932), calcium cyanamide is reacted with caustic to form disodium cyanamide, which is subsequently reacted with allyl bromide to form diallyl cyanamide. This procedure requires considerable manipulations and many processing steps, producing a product of low yield.

Improvements have been suggested through the incorporation of a dipolar aprotic solvent. One such method is disclosed by A. Donetti et al., *Tetrahedron Letters* 39, 3327–8 (1969). This method requires anhydrous cyanamide and dimethyl sulfoxide ion as reagents. A dipolar aprotic solvent was also used by Rider, U.S. Pat. No. 3,692,832, Sept. 19, 1972, in conjunction with alkali metal carbonates or bicarbonates.

SUMMARY OF THE INVENTION

It has now been discovered that improvements in yield and reaction rate are achieved by the use of a phase transfer catalyst in reactions to form disubstituted cyanamides.

In particular, this invention resides in a process for the manufacture of a compound having the formula

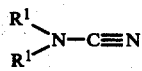

in which $R^1$ is a member selected from the group consisting of $C_1$–$C_6$ alkyl, $C_2$–$C_6$ alkenyl, $C_2$–$C_6$ alkynyl, $C_7$–$C_{10}$ phenylalkyl, and $C_7$–$C_{10}$ halophenylalkyl, which comprises reacting a compound having the formula

in which X is halogen, with cyanamide in the presence of an aqueous solution of an alkali metal or alkaline earth metal hydroxide and a catalytic amount of a catalyst having the formula

in which $R^2$, $R^3$, $R^4$, and $R^5$ are independently $C_1$–$C_{25}$ alkyl, M is selected from the group consisting of nitrogen, phosphorus, and arsenic, and Y is halogen.

Within the scope of the above description, certain embodiments are preferred. In the description of $R^1$, allyl, benzyl, and chlorobenzyl are preferred, with allyl particularly preferred. The term "halogen" as used in the definitions of X and Y is used to designate chlorine, bromine, and iodine. Preferred halogens are chlorine and bromine, with chlorine particularly preferred. In the definition of $R^2$, $R^3$, $R^4$, and $R^5$, $C_1$–$C_{12}$ alkyl is preferred. In the definition of M, nitrogen and phosphorus are preferred, with nitrogen particularly preferred.

DESCRIPTION OF THE PREFERRED EMBODIMENTS

Commercially available grades of cyanamide are suitable for use with the present invention. Aqueous solutions are preferred for reasons of economy and ease of handling. Of these, solutions comprising approximately 10% to approximately 80% by weight are preferred. Solutions comprising 50% by weight are readily available from commercial suppliers.

The terms "alkali metal" and "alkaline earth metal" refer to elements in groups Ia and IIa, respectively of the Periodic Chart of the Elements (*Lange's Handbook of Chemistry*, Revised 10th Ed., McGraw-Hill, 1967). The alkali metals are preferred over the alkaline earth metals. Sodium and potassium, particularly sodium, are the most preferred. As an aqueous solution, the metal hydroxide concentration is not critical and can be varied over a wide range. Preferred concentrations range from about 10% to about 75% by weight, with about 20% to about 50% particularly preferred.

The organic halides represented by the formula $R^1X$ include alkyl, alkenyl, alkynyl, phenylalkyl, and halophenylalkyl halides. The terms "alkyl," "alkenyl," and "alkynyl" include straight chain and branched chain groups. Examples of alkyl groups are methyl, ethyl, isopropyl, and butyl. Examples of alkenyl groups are allyl, 2-methyl-2-propenyl, 2-butenyl, and 3-methyl-2-butenyl. Examples of alkynyl groups are propargyl, 2-butynyl, 3-butynyl, and 4-pentynyl. Examples of phenylalkyl groups are benzyl, phenethyl, and phenylpropyl. Examples of halophenylalkyl groups are p-chlorobenzyl, o-chlorobenzyl, and p-chlorophenethyl.

The catalysts for the present invention are quaternary salts containing a quaternized nitrogen, phosphorus or arsenic atom. The quaternized atom is bonded to four alkyl groups of chain length ranging from 1 to 25 carbon atoms apiece. The alkyl groups on a given quaternized atom can be the same or different, and can have either straight chain or branched chain configurations, within the limits of steric hindrance. Straight alkyl groups are preferred. As quaternized atoms, nitrogen and phosphorus are preferred. Two commercially available examples of ammonium salts are methyltricaprylylammonium chloride and dimethyldicocoammonium chloride. These catalysts are manufactured by General Mills Company, Chemical Division, Kanakee, Illinois. For a further description of methyltricaprylylammonium chloride, see Example 1 below. The "coco" substituent in dimethyldicocoammonium chloride is a mixture of straight chain, saturated and unsaturated alkyl groups of 8 to 18 carbon atoms, with the 12- and 14- carbon chains predominating. This is designated by its manufacturer as "ALIQUAT 221 ®." Examples of quaternary phosphonium salts are tetra-n-butylphosphonium chloride and hexadecyltributylphosphonium bromide.

The reactants are used in approximately stoichiometric proportions, i.e., two moles each of organic halide and metal hydroxide per mole of cyanamide. Any of the reactants may be used in excess. The formation of by-products is slightly greater when a cyanamide excess is used. However, the high cost of many organic halides generally compels the use of excess cyanamide, in spite of the increased by-product formation. Thus, although there is no critical range of relative quantities, mole ratio of cyanamide to organic halide in practical operation ranges from approximately 0.5 to approximately 0.7, where 0.5 is the stoichiometric ratio.

In certain embodiments of the invention, the product is a solid at the reaction temperature. Typical examples of solid products are dibenzyl cyanamide and its halogen substituted analogs. In such cases, an inert solvent which is immiscible with water can be used to dissolve the product. Aliphatic and aromatic hydrocarbons and their chlorinated derivatives are examples of such solvents. Specific examples include toluene, benzene, methylene chloride, 1,2-dichloroethane, and hexane.

The term "catalytic amount" is used herein to represent any amount of catalyst which will facilitate the transfer of a chemical species from one liquid phase to another, and thus enhance the progress of the reaction. In the present invention a metal dianion of cyanamide is formed in the aqueous phase by reaction between the cyanamide and the metal hydroxide. In a likely mechanism, the dianion reacts in the aqueous phase with the quaternary salt catalyst. The result is a displacement of one of the metal cyanamide substitutents with a quaternized anion. The quaternized anion, by virtue of its lipophilic nature, carries the cyanamide ion into the organic phase where it becomes available for reaction with the organic halide. The result is the regeneration of the quaternary salt which redissolves in the aqueous phase, and the simultaneous production of mono-substituted cyanamide, which remains in the organic phase. The latter then reacts with further organic halide to become disubstituted, producing as a by-product a metal salt, which dissolves in the aqueous phase. The amount of catalyst normally ranges from about 0.2 to about 10 mole percent with respect to the cyanamide, preferably from about 0.5 to about 2.0 mole percent.

While the order of addition of the reactants is not critical, it is generally most convenient to add the aqueous metal hydroxide to the cyanamide prior to addition of the organic halide since reaction between the metal hydroxide and the cyanamide is exothermic. For safety of operation and ease of control during the cyanamide/metal hydroxide reaction, it is preferable to maintain a temperature below about 20° C. It is most preferred to maintain the temperature between about 5°-10° C. Once the cyanamide/metal hydroxide reaction is complete, low temperatures need no longer be maintained. The catalyst can be dissolved in the organic halide prior to the addition of the latter to the reaction mixture.

Once the reactants are combined, the reaction will proceed over a wide temperature range. Although there is no critical range, the reaction is most conveniently run between room temperature and the reflux temperature of the reaction mixture. The reaction is preferably run with the system under reflux or at a temperature slightly below reflux. Preferably, the reaction is run between about 50° C. and about 100° C., depending on the boiling temperature of the reaction mixture.

The progress of the reaction can be further enhanced by the use of agitation to increase the contact between the two liquid phases. Agitation may be provided by mechanical stirrers or by the boiling action of the mixture while under reflux. The process of the present invention may be practiced on a batch-wise or on a continuous basis, with suitable provisions for agitation and temperature control. The system pressure is not a critical feature of the invention, and may range from 0.1 to over 10,000 pounds per square inch absolute (psia) (0.1 to 7,000 Newtons per square centimeter, $N/cm^2$), with pressures of from about 1 to about 100 psia preferred (0.7 to 70 $N/cm^2$). Atmospheric pressure is particularly preferred for practical considerations.

The process of the present invention is further illustrated by the following examples.

EXAMPLE 1

N,N-Diallylcyanamide

In this example, the catalytic effect of methyl tricaprylyl ammonium chloride is demonstrated on the reaction between allyl chloride and sodium cyanamide. Methyl tricaprylylammonium chloride is a commercially available product, manufactured by the General Mills Co., Chemical Division, Kankakee, Illinois. The product is commonly referred to by the trade name ALIQUAT ® 336. In this product, the term "caprylyl" designates a mixture of straight chain, saturated alkyl groups of 8 to 10 carbon atoms, with the 8-carbon chain predominating.

Two parallel experiments were run, each using 50.4 grams (g) of a 50 weight % aqueous solution of cyanamide (0.60 mole of cyanamide), 240 g of a 20 weight % aqueous caustic solution (1.20 mole of sodium hydroxide), and 76.5 g (1.0 mole) of allyl chloride. The caustic solution was added by dropping funnel to the cyanamide solution, while the latter was immersed in a bath of dry ice and isopropyl alcohol, maintaining the temperature below 10° C. The allyl chloride was then added, with 5.2 g (0.01 mole) of ALIQUAT ® 336 (methyl tricaprylylammonium chloride) dissolved therein in one of the two experiments.

The reaction flask was then heated to reflux. Samples were taken at 30 minute time intervals and analyzed by gas chromatography. The results are shown below in terms of the conversion of allyl chloride to diallylcyanamide. The figures are expressed in area percent, which is the area under the allyl chloride or diallylcyanamide peak on the chromatogram divided by the total area under both the allyl chloride and diallylcyanamide peaks on the same chromatogram, multiplied by 100. In these analyses, area percents are approximately equivalent to weight percents.

| | Without Catalyst | | With Catalyst | |
|---|---|---|---|---|
| Time from Start of Reflux | Allyl Chloride | Diallyl-Cyanamide | Allyl Chloride | Diallyl-Cyanamide |
| 30 min. | 71.0% | 29.0% | 25.3% | 74.7% |
| 60 min. | 43.8% | 56.2% | 11.9% | 88.1% |
| 90 min. | 28.6% | 71.4% | 4.3% | 95.7% |
| 120 min. | 18.1% | 81.9% | 2.5% | 97.5% |
| 150 min. | 4.7% | 95.3% | | |
| 180 min. | 2.9% | 97.1% | | |
| 210 min. | 3.1% | 96.9% | | |

The catalytic effect is clearly manifest by the sharp increase in reaction rate, as evidenced by the higher values of diallycyanamide concentrations in the first 120 minutes are reflux when the catalyst is used.

EXAMPLE 2

N,N-Diallylcyanamide

This example demonstrates the use of tetrabutyl phosphonium chloride as a catalyst in the preparation of N,N-diallylcyanamide. Following the procedure described in Example 1, the following materials were used:

| | |
|---|---|
| 302 g (3.6 mole) | 50% aqueous cyanamide |
| 576 g (7.2 moles) | 50% aqueous caustic |
| 459 g (6.0 moles) | allyl chloride |
| 17.7 g (0.06 mole) | tetra-n-butyl phosphonium chloride |

Samples of the reaction mixture taken during reflux yielded the following analyses:

| Time from Start of Reflux | Allyl Chloride | Diallylcyanamide |
|---|---|---|
| 30 min. | 33.4% | 65.6% |
| 60 min. | 13.9% | 86.1% |
| 90 min. | 4.5% | 95.5% |

EXAMPLE 3

N,N-Di-(2-methyl-2-propenyl) cyanamide

Following the experimental procedure of Example 1, the following materials were used:

| | |
|---|---|
| 50.4 g (0.6 mole) | 50% aqueous cyanamide |
| 96.0 g (1.2 mole) | 50% aqueous caustic |
| 90.6 g (1.0 mole) | 1-chloro-2-methyl-2-propene |
| 5.2 g | ALIQUAT® 336 |

Samples taken during reflux yielded the following analyses:

| Time from Start of Reflux | 2-Methyl-2-propenyl Chloride | Di-(2-methyl-2-propenyl) cyanamide |
|---|---|---|
| 30 min. | 9.6% | 90.4% |
| 60 min. | 6.8% | 93.2% |

The crude product was distilled through a Vigreaux column 10 centimeters (cm) in length to give the title compound in 79% yield. All yields stated in these examples are based on the alkylating agent.

EXAMPLE 4

N,N-Di-(3-methyl-3-butenyl) cyanamide

The following reagents were mixed at 15°-20° C. and then placed in an oil bath:

| | |
|---|---|
| 50.4 g (0.6 mole) | 50% aqueous cyanamide |
| 96.0 g (1.2 mole) | 50% aqueous caustic |
| 105.0 g (1.0 mole) | 1-chloro-3-methyl-2-butene |
| 5.2 g | ALIQUAT® 336 |

The reaction mixture was maintained at 90° to 95° C. for 2 hours. Water was then added and the organic layer was separated, yielding 94.4 g of an amber colored liquid. The liquid was distilled through a 10 centimeter (cm) Vigreaux column at a pressure of 0.24 torr. Two fractions were taken, excluding the forerun and residue. The boiling point range of the first fraction was 45°-83° C., weighing 6.7 g. The second fraction, weighing 59.1 g, had a boiling point range of 84°-85° C. Nuclear magnetic resonance, infrared spectra and mass spectrometry confirmed the structure of the second fraction as that of the title compound. The yield based on both fractions was 73.8%.

EXAMPLE 5

N,N-Dipropargylcyanamide

The following were mixed at 15°-20° C.:

| | |
|---|---|
| 50.4 g (0.6 mole) | 50% aqueous cyanamide |
| 96.0 g (1.2 mole) | 50% aqueous caustic |
| 119.0 g (1.0 mole) | propargyl bromide |
| 5.2 g | ALIQUAT® 336 |

The reaction mixture was maintained at 50° C. for 1 ½ hours. Water was then added and the organic layer was separated. The crude product weighted 67.5 g and was distilled through a 10 cm Vigreaux column. Three fractions were collected, excluding the forerun and residue, to a combined weight of 31.5 g and a combined yield of 53.3%.

EXAMPLE 6

N,N-Dibenzylcyanamide

Following the experimental procedure in Example 1, the following materials were used:

| | |
|---|---|
| 50.4 g (0.6 mole) | 50% aqueous cyanamide |
| 96.0 g (1.2 mole) | 50% aqueous caustic |
| 126.6 g (1.0 mole) | benzyl chloride |
| 5.2 g | ALIQUAT® 336 |

In addition, 100 milliliters (ml) of toluene was added as a solvent for the benzyl chloride. The reaction mixture was refluxed for 90 minutes, during which time three samples were taken and analyzed by gas chromatography for benzyl chloride and dibenzylcyanamide as follows:

| Time from Start of Reflux | Benzyl Chloride | Dibenzylcyanamide |
|---|---|---|
| 30 min. | 6.5% | 93.5% |
| 60 min. | 2.8% | 97.2% |
| 90 min. | 1.2% | 98.8% |

After 90 minutes of reflux, the reaction mixture was cooled to room temperature and water was added to dissolve the precipitated salt. Following phase separation and extraction of the aqueous phase with further toluene, the solvent was evaporated from the organic solutions to yield a solid residue at room temperature. Recrystallization yielded 63.0 g of a white solid of melting point 52°-53° C. After further recrystallization, the overall yield was 89.7%, with the structure of the product confirmed by infrared and nuclear magnetic resonance spectroscopy.

EXAMPLE 7

N,N-Di-p-chlorobenzylcyanamide

Following the experimental procedure of Example 6, the following materials were refluxed for 90 minutes:

| | |
|---|---|
| 50.4 g (0.6 mole) | 50% aqueous cyanamide |
| 96.0 g (1.2 mole) | 50% aqueous caustic |
| 161.0 g (1.0 mole) | p-chlorobenzyl chloride |
| 5.2 g | ALIQUAT® 336 |
| 100.0 ml | toluene |

Water and further toluene were added after the reflux period. On cooling the reaction mixture to 55° C., a precipitate formed, which was filtered and recrystallized from toluene to yield 105.1 g of a white crystalline solid. After recrystallization, a product was obtained with a melting point of 128°–130° C. The structure was confirmed by infrared, nuclear magnetic resonance, and mass spectrometry as that of the title compound.

EXAMPLE 8

N,N-Di-o-chlorobenzylcyanamide

Following the experimental procedure of Example 6, the following materials were refluxed for 90 minutes:

| | |
|---|---|
| 50.4 g (0.6 mole) | 50% aqueous cyanamide |
| 96.0 g (1.2 mole) | 50% aqueous caustic |
| 161.0 g (1.0 mole) | o-chlorobenzylchloride |
| 5.2 g | ALIQUAT® 336 |
| 100.0 ml | toluene |

After reflux, water was added to dissolve the solid and the mixture was phase separated. After extraction of the aqueous phase, the solvent was evaporated from the organic phase. The yellow residual liquid solidified upon refrigeration, yielding 153.5 g of product. The latter was recrystallized from a mixture of 200 ml of cyclohexane and 50 ml diethyl ether to give 113.2 g of a white solid, with a melting point of 57°–59° C.

EXAMPLE 9

N,N-Di-n-propylacetamide

Following the experimental procedure of Example 1, the following materials were refluxed for 90 minutes:

| | |
|---|---|
| 50.4 g (0.6 mole) | 50% aqueous cyanamide |
| 96.0 g (1.2 mole) | 50% aqueous caustic |
| 123.0 g (1.0 mole) | n-bromopropane |
| 5.2 g | ALIQUAT® 336 |

The crude reaction product was distilled through a 10 cm Vigreaux column at a pressure of 2.8 torr. Three fractions were collected as follows, exclusive of the forerun and residue:

| Fraction | Boiling Point | Weight |
|---|---|---|
| 1 | 23°–63° C. | 4.8 g |
| 2 | 63°–68° C. | 13.9 g |
| 3 | 68°–68.5° C. | 55.0 g |

Gas chromatography analysis of the second and third fractions showed purities of approximately 98% and 100%, respectively, of the title compound. The combined yield of these two fractions was 87.2%.

What is claimed is:

1. A process for the manufacture of a compound having the formula

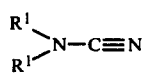

in which $R^1$ is a member selected from the group consisting of $C_1$–$C_6$ alkyl, $C_2$–$C_6$ alkenyl, $C_2$–$C_6$ alkynyl, $C_7$–$C_{10}$ phenylalkyl, and $C_7$–$C_{10}$ halophenylalkyl, which comprises reacting a compound having the formula

in which X is halogen, with cyanamide in the presence of an aqueous solution of an alkali metal or alkaline earth metal hydroxide and a catalytic amount of a catalyst having the formula

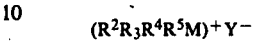

in which $R^2$, $R^3$, $R^4$, and $R^5$ are independently $C_1$–$C_{25}$ alkyl, M is selected from the group consisting of nitrogen, phosphorus, and arsenic, and Y is halogen.

2. A process according to claim 1 in which $R^1$ is $C_2$–$C_6$ alkenyl.

3. A process according to claim 1 in which X is selected from the group consisting of chlorine and bromine.

4. A process according to claim 1 in which $R^1$ is allyl and X is chlorine.

5. A process according to claim 1 in which $R^2$, $R^3$, $R^4$, and $R^5$ are independently $C_1$–$C_{12}$ alkyl, M is selected from the group consisting of nitrogen and phosphorus, and Y is selected from the group consisting of chlorine and bromine.

6. A process according to claim 5 in which Y is chlorine.

7. A process for the manufacture of a compound having the formula

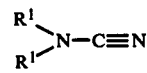

in which $R^1$ is a member selected from the group consisting of $C_1$–$C_6$ alkyl, $C_2$–$C_6$ alkenyl, $C_2$–$C_6$ alkynyl, $C_7$–$C_{10}$ phenylalkyl, and $C_7$–$C_{10}$ halophenylalkyl, which comprises reacting a compound having the formula

in which X is halogen, with cyanamide in the presence of an aqueous solution of an alkali metal hydroxide and a catalytic amount of a catalyst having the formula

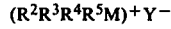

in which $R^2$, $R^3$, $R^4$, and $R^5$ are independently $C_1$–$C_{25}$ alkyl; M is selected from the group consisting of nitrogen, phosphorus, and arsenic; and Y is halogen.

8. A process according to claim 7 in which the alkali metal hydroxide is selected from the group consisting of sodium hydroxide and potassium hydroxide.

9. A process according to claim 7 in which the alkali metal hydroxide is sodium hydroxide.

10. A process according to claims 7, 8, or 9 in which the concentration of the aqueous solution of the alkali metal hydroxide is from about 10% to about 75% by weight.

11. A process according to claims 7, 8, or 9 in which the concentration of the aqueous solution of the alkali metal hydroxide is from about 20% to about 50% by weight.

* * * * *